United States Patent
Nutting

(10) Patent No.: US 10,080,605 B2
(45) Date of Patent: *Sep. 25, 2018

(54) DEPLOYMENT MECHANISMS FOR SURGICAL INSTRUMENTS

(71) Applicant: COVIDIEN LP, Mansfield, MA (US)

(72) Inventor: Judd C. Nutting, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 494 days.

This patent is subject to a terminal disclaimer.

(21) Appl. No.: 14/798,016

(22) Filed: Jul. 13, 2015

(65) Prior Publication Data

US 2016/0074097 A1    Mar. 17, 2016

Related U.S. Application Data

(60) Provisional application No. 62/051,376, filed on Sep. 17, 2014.

(51) Int. Cl.
*A61B 18/14* (2006.01)
*A61B 18/12* (2006.01)
(Continued)

(52) U.S. Cl.
CPC ...... *A61B 18/1445* (2013.01); *A61B 17/2909* (2013.01); *A61B 18/1482* (2013.01);
(Continued)

(58) Field of Classification Search
CPC ............ A61B 18/1445; A61B 17/2909; A61B 18/1482; A61B 17/29; A61B 17/295;
(Continued)

(56) References Cited

U.S. PATENT DOCUMENTS

| 4,005,714 A | 2/1977 | Hiltebrandt |
| D249,549 S | 9/1978 | Pike |

(Continued)

FOREIGN PATENT DOCUMENTS

| AU | 2011253698 A1 | 12/2011 |
| CN | 21299462 | 9/2009 |

(Continued)

OTHER PUBLICATIONS

U.S. Appl. No. 08/926,869, James G. Chandler.

(Continued)

*Primary Examiner* — Jaymi Della

(57) ABSTRACT

An electrosurgical instrument includes a housing, a shaft extending from the housing, and an end effector assembly attached at a distal end of the shaft. A handle assembly is coupled to the housing and includes a movable handle for manipulating the end effector assembly. An outer sleeve is disposed about the shaft and selectively translatable relative thereto. An energizable member is operably coupled to the outer sleeve. A deployment mechanism is provided including a lever rotatably coupled to the housing and positioned proximally of the movable handle and at least one link member coupled between the lever and the outer sleeve. The link member(s) couple to the outer sleeve distally of the movable handle. Rotation of the lever translates the outer sleeve distally to move the outer sleeve over the end effector assembly and simultaneously deploy the energizable member distally past the end effector assembly.

20 Claims, 12 Drawing Sheets

(51) Int. Cl.
  *A61B 17/29* (2006.01)
  *A61B 18/00* (2006.01)
  *A61B 17/295* (2006.01)
  *A61B 17/00* (2006.01)

(52) U.S. Cl.
  CPC ............ *A61B 17/29* (2013.01); *A61B 17/295* (2013.01); *A61B 2017/00336* (2013.01); *A61B 2017/292* (2013.01); *A61B 2017/2919* (2013.01); *A61B 2017/2925* (2013.01); *A61B 2018/0063* (2013.01); *A61B 2018/00196* (2013.01); *A61B 2018/00577* (2013.01); *A61B 2018/00589* (2013.01); *A61B 2018/00595* (2013.01); *A61B 2018/00922* (2013.01); *A61B 2018/00952* (2013.01); *A61B 2018/00958* (2013.01); *A61B 2018/126* (2013.01); *A61B 2018/1253* (2013.01); *A61B 2018/1475* (2013.01)

(58) Field of Classification Search
  CPC .. A61B 2017/00336; A61B 2017/2919; A61B 2017/292; A61B 2017/2925; A61B 2018/00196; A61B 2018/00577; A61B 2018/00589; A61B 2018/00595; A61B 2018/0063; A61B 2018/00922; A61B 2018/00952; A61B 2018/00958; A61B 2018/1253; A61B 2018/126; A61B 2018/1475
  See application file for complete search history.

(56) References Cited

U.S. PATENT DOCUMENTS

| | | | |
|---|---|---|---|
| D263,020 | S | 2/1982 | Rau, III |
| D295,893 | S | 5/1988 | Sharkany et al. |
| D295,894 | S | 5/1988 | Sharkany et al. |
| D298,353 | S | 11/1988 | Manno |
| D299,413 | S | 1/1989 | DeCarolis |
| 5,026,379 | A | 6/1991 | Yoon |
| D343,453 | S | 1/1994 | Noda |
| 5,312,391 | A | 5/1994 | Wilk |
| 5,318,589 | A | 6/1994 | Lichtman |
| 5,324,254 | A | 6/1994 | Phillips |
| D348,930 | S | 7/1994 | Olson |
| D349,341 | S | 8/1994 | Lichtman et al. |
| 5,342,359 | A | 8/1994 | Rydell |
| 5,368,600 | A | 11/1994 | Failla et al. |
| D354,564 | S | 1/1995 | Medema |
| 5,401,274 | A | 3/1995 | Kusunoki |
| D358,887 | S | 5/1995 | Feinberg |
| 5,411,519 | A | 5/1995 | Tovey et al. |
| 5,445,638 | A | 8/1995 | Rydell et al. |
| 5,458,598 | A | 10/1995 | Feinberg et al. |
| 5,527,313 | A | 6/1996 | Scott et al. |
| 5,556,397 | A | 9/1996 | Long et al. |
| 5,611,813 | A | 3/1997 | Lichtman |
| D384,413 | S | 9/1997 | Zlock et al. |
| 5,665,100 | A * | 9/1997 | Yoon .................. A61B 10/06 606/139 |
| 5,735,873 | A | 4/1998 | MacLean |
| H1745 | H | 8/1998 | Paraschac |
| 5,792,164 | A | 8/1998 | Lakatos et al. |
| 5,807,393 | A | 9/1998 | Williamson, IV et al. |
| D402,028 | S | 12/1998 | Grimm et al. |
| D408,018 | S | 4/1999 | McNaughton |
| 5,893,863 | A | 4/1999 | Yoon |
| 5,919,202 | A | 7/1999 | Yoon |
| D416,089 | S | 11/1999 | Barton et al. |
| 6,004,319 | A | 12/1999 | Goble et al. |
| D424,694 | S | 5/2000 | Tetzlaff et al. |
| D425,201 | S | 5/2000 | Tetzlaff et al. |
| 6,113,596 | A | 9/2000 | Hooven et al. |
| H1904 | H | 10/2000 | Yates et al. |
| 6,156,009 | A | 12/2000 | Grabek |
| 6,190,386 | B1 | 2/2001 | Rydell |
| 6,270,497 | B1 | 8/2001 | Sekino et al. |
| D449,886 | S | 10/2001 | Tetzlaff et al. |
| 6,299,625 | B1 | 10/2001 | Bacher |
| D453,923 | S | 2/2002 | Olson |
| D454,951 | S | 3/2002 | Bon |
| D457,958 | S | 5/2002 | Dycus et al. |
| D457,959 | S | 5/2002 | Tetzlaff et al. |
| 6,387,094 | B1 | 5/2002 | Eitenmuller |
| H2037 | H | 7/2002 | Yates et al. |
| D465,281 | S | 11/2002 | Lang |
| D466,209 | S | 11/2002 | Bon |
| 6,551,313 | B1 | 4/2003 | Levin |
| 6,558,385 | B1 | 5/2003 | McClurken et al. |
| 6,679,882 | B1 | 1/2004 | Kornerup |
| D493,888 | S | 8/2004 | Reschke |
| D496,997 | S | 10/2004 | Dycus et al. |
| 6,808,525 | B2 | 10/2004 | Latterell et al. |
| D499,181 | S | 11/2004 | Dycus et al. |
| 6,837,888 | B2 | 1/2005 | Ciarrocca et al. |
| D502,994 | S | 3/2005 | Blake, III |
| D509,297 | S | 9/2005 | Wells |
| 6,942,662 | B2 | 9/2005 | Goble et al. |
| 7,033,356 | B2 | 4/2006 | Latterell et al. |
| 7,063,699 | B2 | 6/2006 | Hess et al. |
| D525,361 | S | 7/2006 | Hushka |
| D531,311 | S | 10/2006 | Guerra et al. |
| 7,128,254 | B2 | 10/2006 | Shelton, IV et al. |
| D533,274 | S | 12/2006 | Visconti et al. |
| D533,942 | S | 12/2006 | Kerr et al. |
| D535,027 | S | 1/2007 | James et al. |
| D538,932 | S | 3/2007 | Malik |
| D541,418 | S | 4/2007 | Schechter et al. |
| 7,208,005 | B2 | 4/2007 | Frecker et al. |
| D541,611 | S | 5/2007 | Aglassinger |
| D541,938 | S | 5/2007 | Kerr et al. |
| D545,432 | S | 6/2007 | Watanabe |
| 7,232,440 | B2 | 6/2007 | Dumbauld et al. |
| D547,154 | S | 7/2007 | Lee |
| D564,662 | S | 3/2008 | Moses et al. |
| D567,943 | S | 4/2008 | Moses et al. |
| 7,367,976 | B2 | 5/2008 | Lawes et al. |
| 7,402,162 | B2 | 7/2008 | Ouchi |
| D575,395 | S | 8/2008 | Hushka |
| D575,401 | S | 8/2008 | Hixson et al. |
| 7,442,194 | B2 | 10/2008 | Dumbauld et al. |
| 7,445,621 | B2 | 11/2008 | Dumbauld et al. |
| D582,038 | S | 12/2008 | Swoyer et al. |
| 7,481,810 | B2 | 1/2009 | Dumbauld et al. |
| 7,510,562 | B2 | 3/2009 | Lindsay |
| 7,588,570 | B2 | 9/2009 | Wakikaido et al. |
| 7,658,311 | B2 | 2/2010 | Boudreaux |
| D617,900 | S | 6/2010 | Kingsley et al. |
| D617,901 | S | 6/2010 | Unger et al. |
| D617,902 | S | 6/2010 | Twomey et al. |
| D617,903 | S | 6/2010 | Unger et al. |
| D618,798 | S | 6/2010 | Olson et al. |
| 7,758,577 | B2 | 7/2010 | Nobis et al. |
| D621,503 | S | 8/2010 | Otten et al. |
| 7,789,878 | B2 | 9/2010 | Dumbauld et al. |
| 7,815,636 | B2 | 10/2010 | Ortiz |
| 7,819,872 | B2 | 10/2010 | Johnson et al. |
| D627,462 | S | 11/2010 | Kingsley |
| D628,289 | S | 11/2010 | Romero |
| D628,290 | S | 11/2010 | Romero |
| D630,324 | S | 1/2011 | Reschke |
| 7,879,035 | B2 | 2/2011 | Garrison et al. |
| D649,249 | S | 11/2011 | Guerra |
| D649,643 | S | 11/2011 | Allen, IV et al. |
| D661,394 | S | 6/2012 | Romero et al. |
| 8,257,352 | B2 | 9/2012 | Lawes et al. |
| 8,333,765 | B2 | 12/2012 | Johnson et al. |
| 8,353,437 | B2 | 1/2013 | Boudreaux |
| 8,454,602 | B2 | 6/2013 | Kerr et al. |
| 8,523,898 | B2 | 9/2013 | Bucciaglia et al. |
| 8,529,566 | B2 | 9/2013 | Kappus et al. |
| 8,568,408 | B2 | 10/2013 | Townsend et al. |
| 8,591,510 | B2 | 11/2013 | Allen, IV et al. |

(56) References Cited

U.S. PATENT DOCUMENTS

| | | |
|---|---|---|
| 8,628,557 B2 | 1/2014 | Collings et al. |
| 8,679,098 B2 | 3/2014 | Hart |
| 8,679,140 B2 | 3/2014 | Butcher |
| RE44,834 E | 4/2014 | Dumbauld et al. |
| 8,685,009 B2 | 4/2014 | Chernov et al. |
| 8,685,056 B2 | 4/2014 | Evans et al. |
| 8,696,667 B2 | 4/2014 | Guerra et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,413 B2 | 6/2014 | Dycus |
| 8,747,434 B2 | 6/2014 | Larson et al. |
| 8,752,264 B2 | 6/2014 | Ackley et al. |
| 8,756,785 B2 | 6/2014 | Allen, IV et al. |
| 8,845,636 B2 | 9/2014 | Allen, IV et al. |
| 8,852,185 B2 | 10/2014 | Twomey |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,900,232 B2 | 12/2014 | Ourada |
| 8,920,461 B2 | 12/2014 | Unger et al. |
| 8,939,972 B2 | 1/2015 | Twomey |
| 8,961,513 B2 | 2/2015 | Allen, IV et al. |
| 8,961,514 B2 | 2/2015 | Garrison |
| 8,961,515 B2 | 2/2015 | Twomey et al. |
| 8,968,283 B2 | 3/2015 | Kharin |
| 8,968,298 B2 | 3/2015 | Twomey |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Homer et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,492 B2 | 5/2015 | Kerr et al. |
| 9,033,981 B2 | 5/2015 | Olson et al. |
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,060,780 B2 | 6/2015 | Twomey et al. |
| 9,072,524 B2 | 7/2015 | Heard et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,161,807 B2 | 10/2015 | Garrison |
| 2002/0049442 A1 | 4/2002 | Roberts et al. |
| 2004/0236326 A1 | 11/2004 | Schulze et al. |
| 2005/0113827 A1* | 5/2005 | Dumbauld ......... A61B 18/1445 606/45 |
| 2005/0187547 A1 | 8/2005 | Sugi |
| 2006/0129146 A1 | 6/2006 | Dycus et al. |
| 2007/0078458 A1 | 4/2007 | Dumbauld et al. |
| 2007/0106295 A1 | 5/2007 | Garrison et al. |
| 2007/0213707 A1 | 9/2007 | Dumbauld et al. |
| 2007/0278277 A1 | 12/2007 | Wixey et al. |
| 2008/0083813 A1 | 4/2008 | Zemlok et al. |
| 2008/0215050 A1 | 9/2008 | Bakos |
| 2008/0243120 A1 | 10/2008 | Lawes et al. |
| 2009/0012556 A1 | 1/2009 | Boudreaux et al. |
| 2009/0112206 A1 | 4/2009 | Dumbauld et al. |
| 2009/0125026 A1 | 5/2009 | Rioux et al. |
| 2009/0125027 A1* | 5/2009 | Fischer ............... A61B 17/3203 606/46 |
| 2009/0131974 A1 | 5/2009 | Pedersen et al. |
| 2009/0171350 A1 | 7/2009 | Dycus et al. |
| 2009/0182327 A1 | 7/2009 | Unger |
| 2009/0254084 A1 | 10/2009 | Naito |
| 2010/0185196 A1 | 7/2010 | Sakao et al. |
| 2010/0185197 A1 | 7/2010 | Sakao et al. |
| 2010/0292690 A1 | 11/2010 | Livneh |
| 2011/0071525 A1 | 3/2011 | Dumbauld et al. |
| 2011/0087218 A1 | 4/2011 | Boudreaux et al. |
| 2011/0130757 A1 | 6/2011 | Horlle et al. |
| 2011/0264093 A1 | 10/2011 | Schall |
| 2011/0276049 A1 | 11/2011 | Gerhardt |
| 2011/0319886 A1 | 12/2011 | Chojin et al. |
| 2012/0083827 A1 | 4/2012 | Artale et al. |
| 2012/0209263 A1 | 8/2012 | Sharp et al. |
| 2012/0239034 A1 | 9/2012 | Horner et al. |
| 2012/0259331 A1 | 10/2012 | Garrison |
| 2012/0265241 A1 | 10/2012 | Hart et al. |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296323 A1 | 11/2012 | Chernov et al. |
| 2012/0296371 A1 | 11/2012 | Kappus et al. |
| 2012/0303026 A1 | 11/2012 | Dycus et al. |
| 2012/0323238 A1 | 12/2012 | Tyrrell et al. |
| 2012/0330308 A1 | 12/2012 | Joseph |
| 2012/0330351 A1 | 12/2012 | Friedman et al. |
| 2013/0018364 A1 | 1/2013 | Chernov et al. |
| 2013/0022495 A1 | 1/2013 | Allen, IV et al. |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0138101 A1 | 5/2013 | Kerr |
| 2013/0144284 A1 | 6/2013 | Behnke, II et al. |
| 2013/0165907 A1* | 6/2013 | Attar .................. A61B 17/29 606/1 |
| 2013/0197503 A1 | 8/2013 | Orszulak |
| 2013/0218198 A1 | 8/2013 | Larson et al. |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |

(56) References Cited

U.S. PATENT DOCUMENTS

| | | |
|---|---|---|
| 2014/0100564 A1 | 4/2014 | Garrison |
| 2014/0100568 A1 | 4/2014 | Garrison |
| 2014/0135758 A1 | 5/2014 | Mueller |
| 2014/0276797 A1 | 9/2014 | Batchelor et al. |

FOREIGN PATENT DOCUMENTS

| | | |
|---|---|---|
| CN | 201299462 | 9/2009 |
| CN | 101636120 A | 1/2010 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 4242143 A1 | 6/1994 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 20 2007 009317 U1 | 8/2007 |
| DE | 202007009165 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1530952 | 5/2005 |
| EP | 2842509 A1 | 3/2015 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 02/45589 A2 | 6/2002 |
| WO | 2005/110264 A2 | 11/2005 |
| WO | 2006021269 A1 | 3/2006 |
| WO | 05110264 A3 | 4/2006 |
| WO | 2007118608 A1 | 10/2007 |
| WO | 08/040483 A1 | 4/2008 |
| WO | 2011/018154 A1 | 2/2011 |

OTHER PUBLICATIONS

U.S. Appl. No. 09/177,950, Randel A. Frazier.
U.S. Appl. No. 09/387,883, Dale F. Schmaltz.
U.S. Appl. No. 09/591,328, Thomas P. Ryan.
U.S. Appl. No. 12/336,970, Paul R. Sremcich.
Michael Choti, "Abdominoperineal Resection with the LigaSure Vessel Sealing System and LigaSure Atlas 20 cm Open Instrument"; Innovations That Work, Jun. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
E. David Crawford "Evaluation of a New Vessel Sealing Device in Urologic Cancer Surgery", 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. TT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
LigaSure Vessel Sealing System, the Seal of Confidence in General, Gynecologic, Urologic, and Laparoscopic Surgery; Sales/Product Literature; Apr. 2002.

(56) References Cited

OTHER PUBLICATIONS

Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room", 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex", 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
European Search report issued in corresponding application No. 15178242.2 dated Mar. 14, 2016.
W. Scott Helton, "LigaSure Vessel Sealing System: Revolutionary Hemostasis Product for General Surgery"; Sales/Product Literature 1999.
Levy et al., "Update on Hysterectomy—New Technologies and Techniques" OBG Management, Feb. 2003.

* cited by examiner

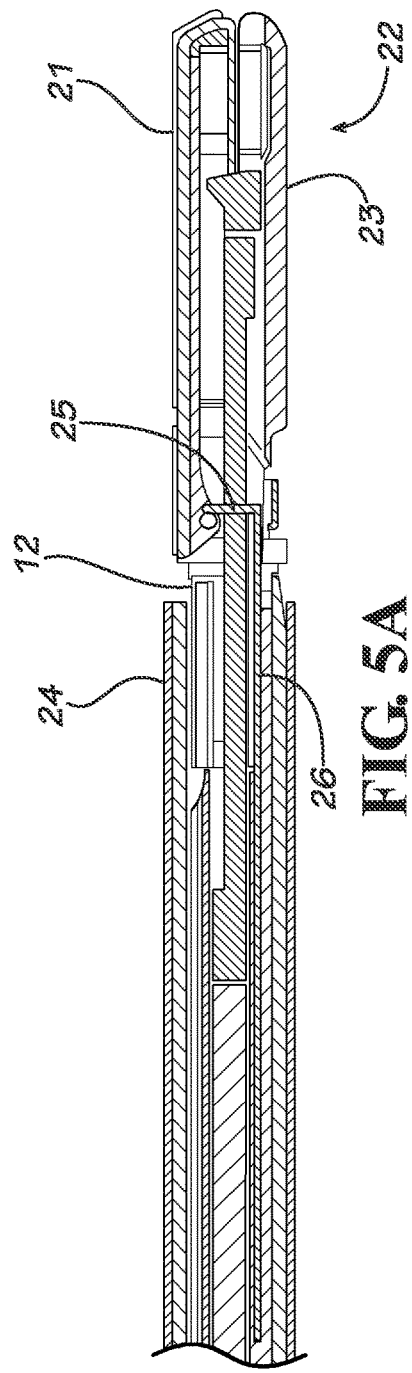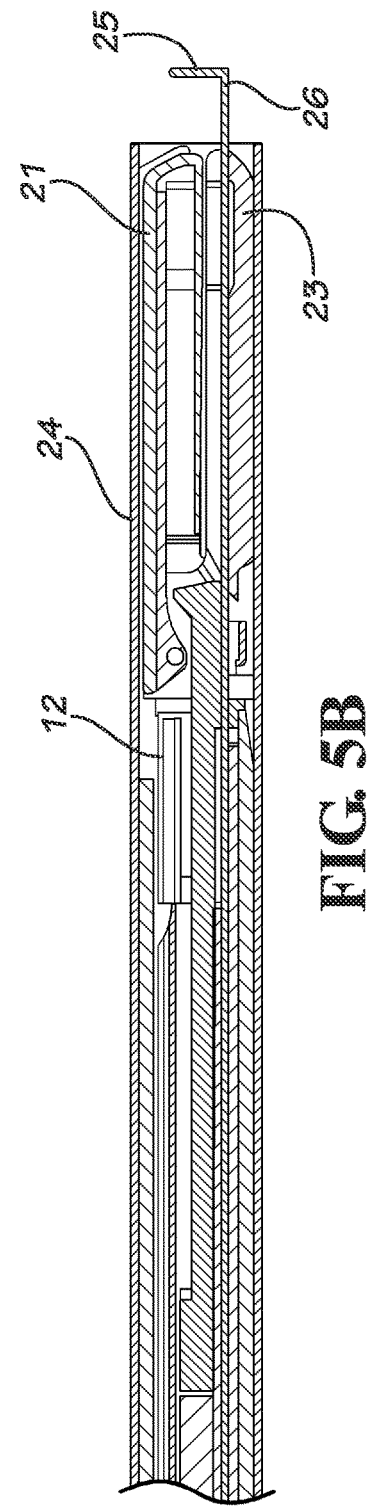
FIG. 5A
FIG. 5B

DEPLOYMENT MECHANISMS FOR SURGICAL INSTRUMENTS

CROSS REFERENCE TO RELATED APPLICATION

The present application claims the benefit of and priority to U.S. Provisional Application Ser. No. 62/051,376, filed on Sep. 17, 2014, the entire contents of which are incorporated herein by reference.

BACKGROUND

Technical Field

The present disclosure relates to deployment mechanisms for surgical instruments. More particularly, the present disclosure relates to deployment mechanisms for multi-functional surgical instruments.

Background of Related Art

Many surgical instruments include one or more movable handles, levers, actuators, triggers, etc. for actuating and/or manipulating one or more functional components of the surgical instrument. For example, a surgical forceps may include a movable handle that is selectively compressible relative to a stationary handle for moving first and second jaw members of the forceps between spaced-apart and approximated positions for grasping tissue therebetween. Such a forceps may further include a trigger for selectively deploying a knife between the jaw members to cut tissue grasped therebetween.

As can be appreciated, as additional functional components are added to the surgical instrument, additional deployment structures or deployment structures capable of actuating more than one component are required. However, multiple deployment structures and/or combined deployment structures may be limited by spatial constraints within the housing of the surgical instrument, functional constraints of the components (e.g., where a combined deployment structure imparts additional force requirements for deploying one or more of the components coupled thereto), and/or may overly complicate the operable components of the surgical instrument.

SUMMARY

In view of the foregoing, deployment mechanisms that are configured for use with multi-functional surgical instruments that are operable in bipolar and/or monopolar modes of operation, and which are easy to operate and inexpensive to manufacture may prove useful in the surgical arena.

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is an electrosurgical instrument including a housing, a shaft extending distally from the housing, an end effector assembly attached to a distal end of the shaft, and a handle assembly coupled to the housing. The handle assembly includes a movable handle operable to manipulate the end effector assembly. The instrument further includes an outer sleeve disposed about and selectively translatable relative to the shaft, an energizable member operably coupled to the outer sleeve, and a deployment mechanism operably coupled to the housing. The deployment mechanism includes a lever rotatably coupled to the housing and positioned proximally of the movable handle and one or more link members coupled between the lever and the outer sleeve. The one or more link members are coupled to the outer sleeve distally of the movable handle. In use, rotation of the lever relative to the housing moves the one or more link members, which, in turn, translates the outer sleeve distally to move the outer sleeve over the end effector assembly and simultaneously deploy the energizable member distally past the end effector assembly.

In an aspect of the present disclosure, a collar is operably disposed on a proximal end of the outer sleeve. The collar is pivotably coupled to the one or more link members.

In another aspect of the present disclosure, first and second link members are provided. In such aspects a first pivot pin pivotably couples a distal end of the second link member to the collar of the outer sleeve. Further, a proximal end of the first link member may be pivotably coupled to the lever and a distal end of the first link may be pivotably coupled to a proximal end of the second link member via a second pivot pin.

In yet another aspect of the present disclosure, an elongated slot is defined in the housing and extends from an interior wall of the housing. The elongated slot operably receives the second pivot pin. Further, the second pivot pin may be configured to translate within the elongated slot when the lever is rotated relative to the housing to guide movement of the first and second link members.

In still another aspect of the present disclosure, the lever is rotatable between a first configuration, wherein the outer sleeve and energizable member are disposed in retracted positions, and a second configuration, wherein the outer sleeve and energizable member are disposed in deployed positions.

In still yet another aspect of the present disclosure, the lever includes a body portion disposed within the housing and a paddle portion extending from the body portion through an opening in the housing to permit manipulation thereof from an exterior of the housing.

In another aspect of the present disclosure, the end effector assembly is configured for treating tissue with bipolar energy and the energizable member is configured for treating tissue with monopolar energy.

Provided in accordance with other aspects of the present disclosure is an electrosurgical instrument including a housing, a shaft extending distally from the housing, and an end effector assembly attached at a distal end of the shaft. An outer sleeve is disposed about the shaft and selectively translatable relative to the shaft. An energizable member is operably coupled to the outer sleeve. A deployment mechanism is operably coupled to the housing and includes a lever rotatably coupled to the housing via an axle, and first, second, and third link members. The first link member is pivotably coupled to the axle at a fixed end thereof and defines a free end. The second link member is pivotably coupled to the housing at a fixed end thereof and coupled to the deployable assembly at a free end thereof. The second link member defines an intermediate portion disposed between the fixed and free ends. A third link member is pivotably coupled between the fixed end of the first link member and the intermediate portion of the second link member. In use, rotation of the lever about the axle pivots the first and second link members about the respective fixed ends thereof and effects movement of the third link member, thereby translating the outer sleeve distally over the end effector assembly and simultaneously deploying the energizable member distally past the end effector assembly.

In an aspect of the present disclosure, the first link member includes a bifurcated configuration having an opening defined therein that is configured to receive the outer sleeve therebetween.

In another aspect of the present disclosure, the second link member includes a bifurcated configuration having opposing finger portions each defining an elongated slot configured to receive at least a portion of a pivot pin coupled to the outer sleeve.

In still another aspect of the present disclosure, the lever is rotatable between a first configuration, wherein the outer sleeve and energizable member are disposed in retracted positions, and a second configuration, wherein the outer sleeve and energizable member are disposed in deployed positions.

In yet another aspect of the present disclosure, the end effector assembly is configured for treating tissue with bipolar energy and the energizable member is configured for treating tissue with monopolar energy.

In still yet another aspect of the present disclosure, the lever includes a body portion disposed within the housing and a paddle portion extending from the body portion through an opening in the housing to permit manipulation thereof from an exterior of the housing.

Provided in accordance with other aspects of the present disclosure is an electrosurgical instrument including a housing, a shaft extending distally from the housing, and an end effector assembly attached at a distal end of the shaft. An outer sleeve is disposed about the shaft and selectively translatable relative to the shaft. An energizable member is operably coupled to the outer sleeve. A deployment mechanism is operably coupled to the housing and includes a lever rotatably coupled to the housing via an axle, a first link member, and a second link member. The first link member is pivotably coupled to the axle at a fixed end thereof and defines a free end. The second link member is pivotably coupled to the housing at a fixed end thereof and coupled to the deployable assembly at a free end thereof. The second link member defines an intermediate portion disposed between the fixed and free ends. The free end of the first link member is pivotably coupled to the intermediate portion of the second link member. In use, rotation of the lever about the axle pivots the first and second link members about the respective fixed ends thereof, thereby translating the outer sleeve distally over the end effector assembly and simultaneously deploying the energizable member distally past the end effector assembly.

In another aspect of the present disclosure, the second link member includes a bifurcated configuration having opposing finger portions each defining an elongated slot configured to receive at least a portion of a pivot pin coupled to the outer sleeve.

In still another aspect of the present disclosure, the lever is rotatable between a first configuration, wherein the outer sleeve and energizable member are disposed in retracted positions, and a second configuration, wherein the outer sleeve and energizable member are disposed in deployed positions.

In yet another aspect of the present disclosure, the end effector assembly is configured for treating tissue with bipolar energy and the energizable member is configured for treating tissue with monopolar energy.

In still yet another aspect of the present disclosure, the lever includes a body portion disposed within the housing and a paddle portion extending from the body portion through an opening in the housing to permit manipulation thereof from an exterior of the housing.

BRIEF DESCRIPTION OF THE DRAWINGS

Various aspects of the present disclosure are described herein with reference to the drawings wherein like reference numerals identify similar or identical elements:

FIG. 5A is a cross-sectional view of a distal end of the endoscopic surgical forceps with a monopolar electrode, which is connected to the deployment mechanism shown in FIGS. 2 and 3, shown in the retracted configuration;

FIG. 5B is a cross-sectional view of the distal end of the endoscopic surgical forceps with the monopolar electrode of FIG. 5A shown in the deployed configuration;

DETAILED DESCRIPTION

Figure 1:
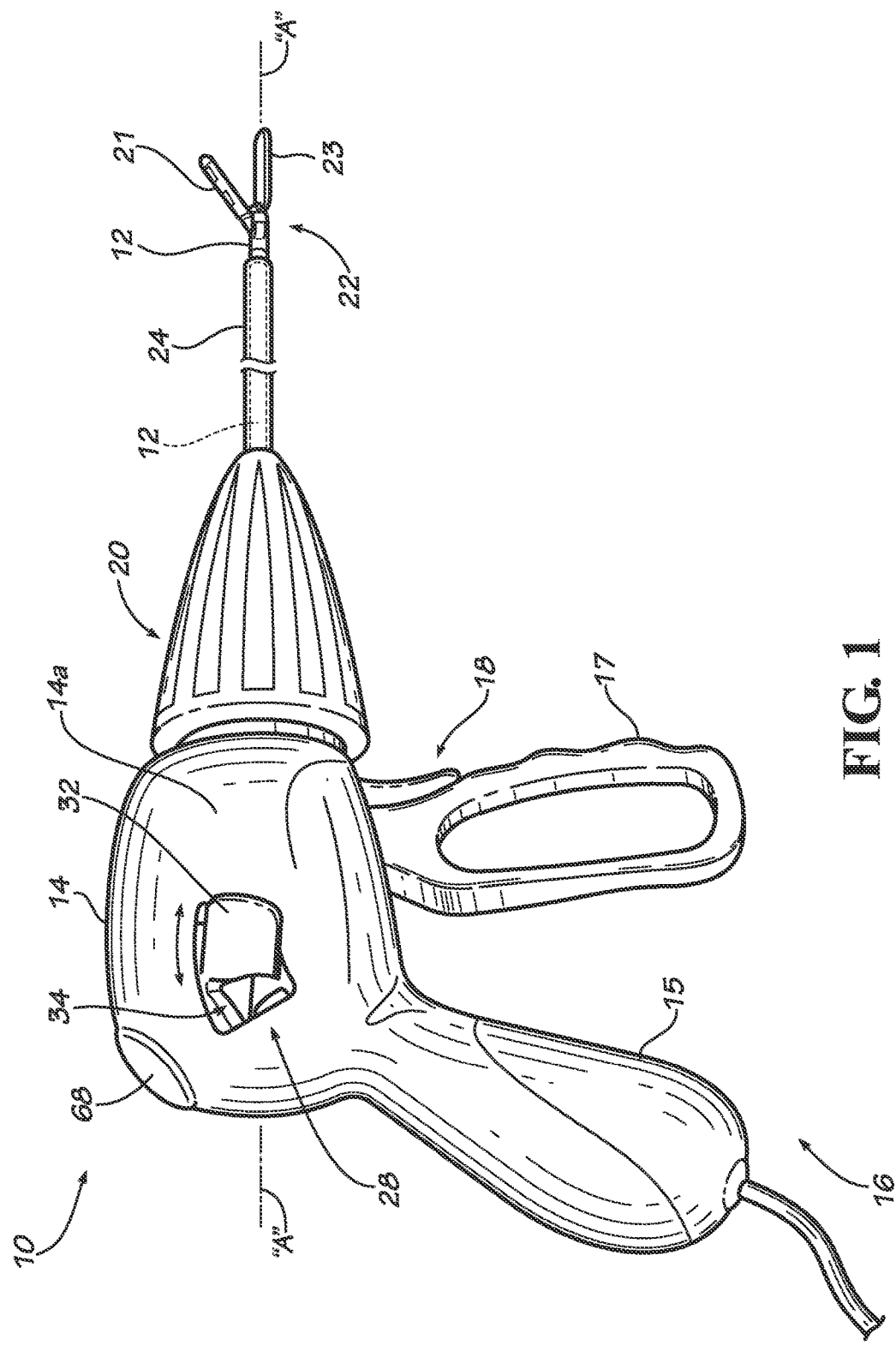
FIG. 1 is a side, right perspective view of an endoscopic surgical forceps in accordance with an embodiment of the present disclosure.

Deployment mechanisms that are configured for use with multi-functional surgical instruments that are operable in bipolar and/or monopolar modes of operation may prove useful in the surgical arena, and such deployment mechanisms are described herein. Specifically, the deployment mechanisms described herein include one or more linkage configurations that, when actuated, move a monopolar electrode of the electrosurgical forceps from a retracted configuration to a deployed configuration to electrosurgically treat tissue.

FIGS. 1-4 illustrate a forceps 10 that includes a deployment mechanism 28 in accordance with an embodiment of the present disclosure. The forceps 10 is configured to operate in both a bipolar mode, e.g., for grasping, treating, coagulating and/or sealing tissue, and a monopolar mode, e.g., for treating and/or dissecting tissue, although other configurations are also contemplated.

Briefly, the forceps 10 includes an outer fixed shaft 12 defining a longitudinal axis "A-A," a housing 14, a handle assembly 16, a trigger assembly 18 (only shown in FIG. 1), a rotating assembly 20, an end effector assembly 22, and a monopolar assembly that includes an outer sleeve 24 and an energizable rod member 26 (the energizable rod 26 is shown in FIG. 5B). For a more detailed description of the forceps 10 and operative components associated therewith, reference is made to commonly-owned U.S. patent application Ser. No. 14/047,474.

Figure 2:
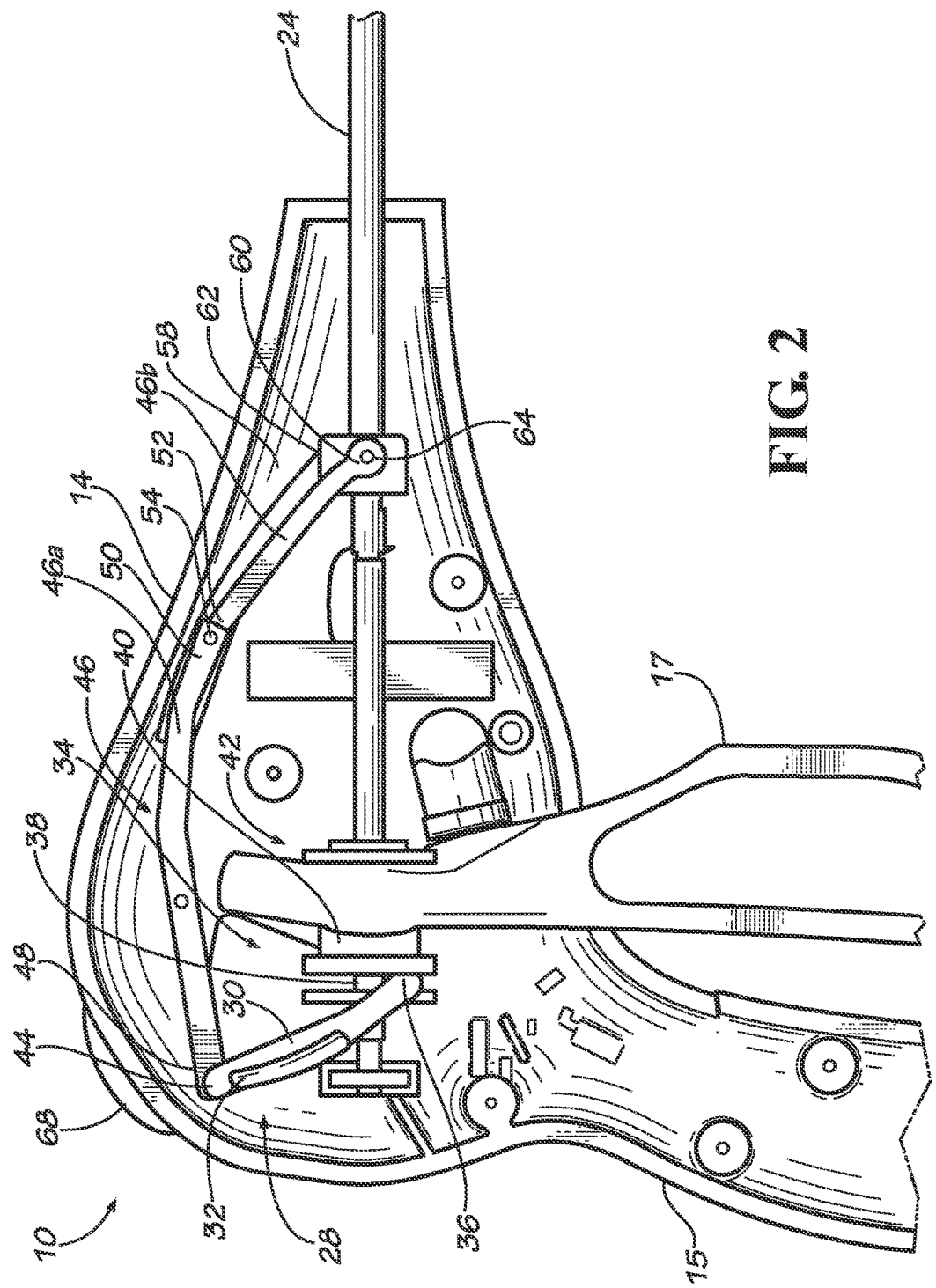
FIG. 2 is a partial, cut-away view of a proximal end of the endoscopic surgical forceps shown in FIG. 1 with a deployment mechanism of the endoscopic surgical forceps shown in a retracted configuration.
Figure 3:
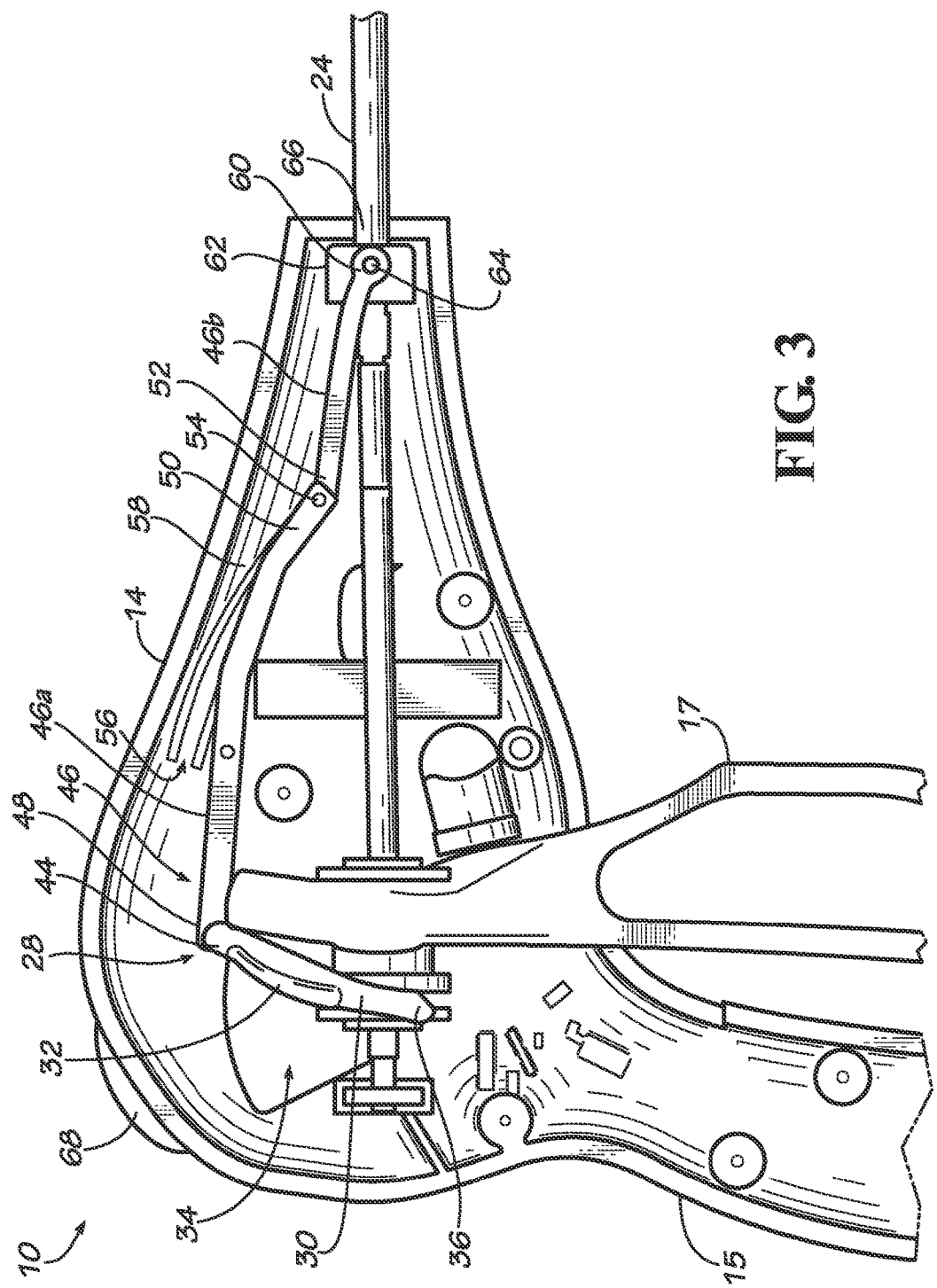
FIG. 3 is a partial, cut-away view of the proximal end of the endoscopic surgical forceps with the deployment mechanism shown in a deployed configuration.
Figure 4:
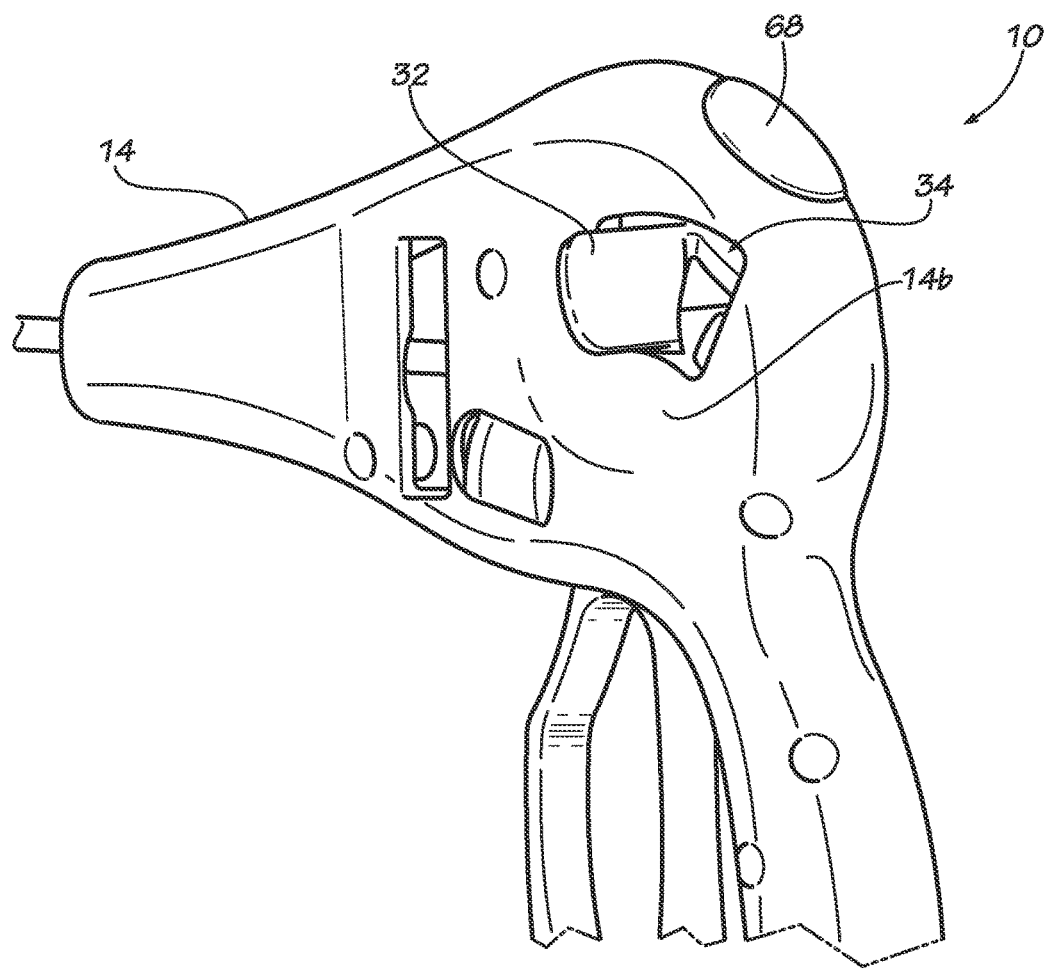
FIG. 4 is a partial, left perspective view of the proximal end of the endoscopic surgical forceps with a thumb paddle of the deployment mechanism shown in the deployed configuration.
Figure 6:
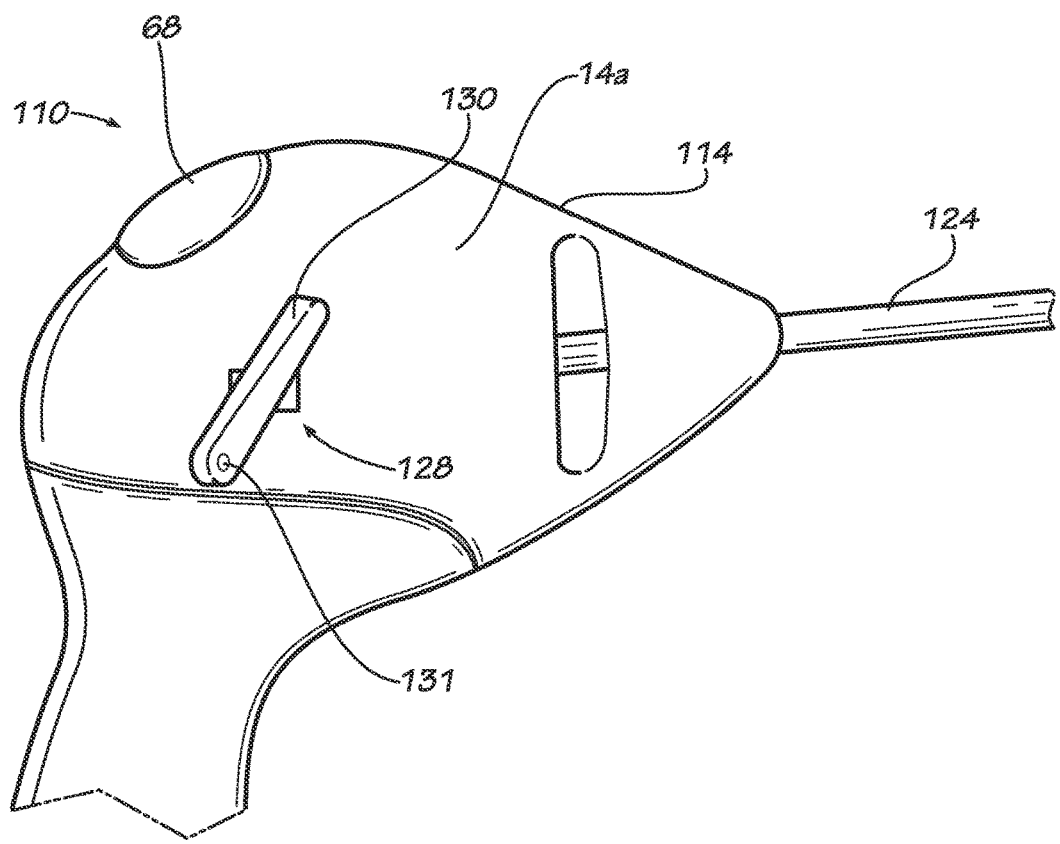
FIG. 6 is a partial, perspective view of a proximal end of an endoscopic surgical forceps including a deployment mechanism in accordance with another embodiment of the present disclosure.
Figure 7:
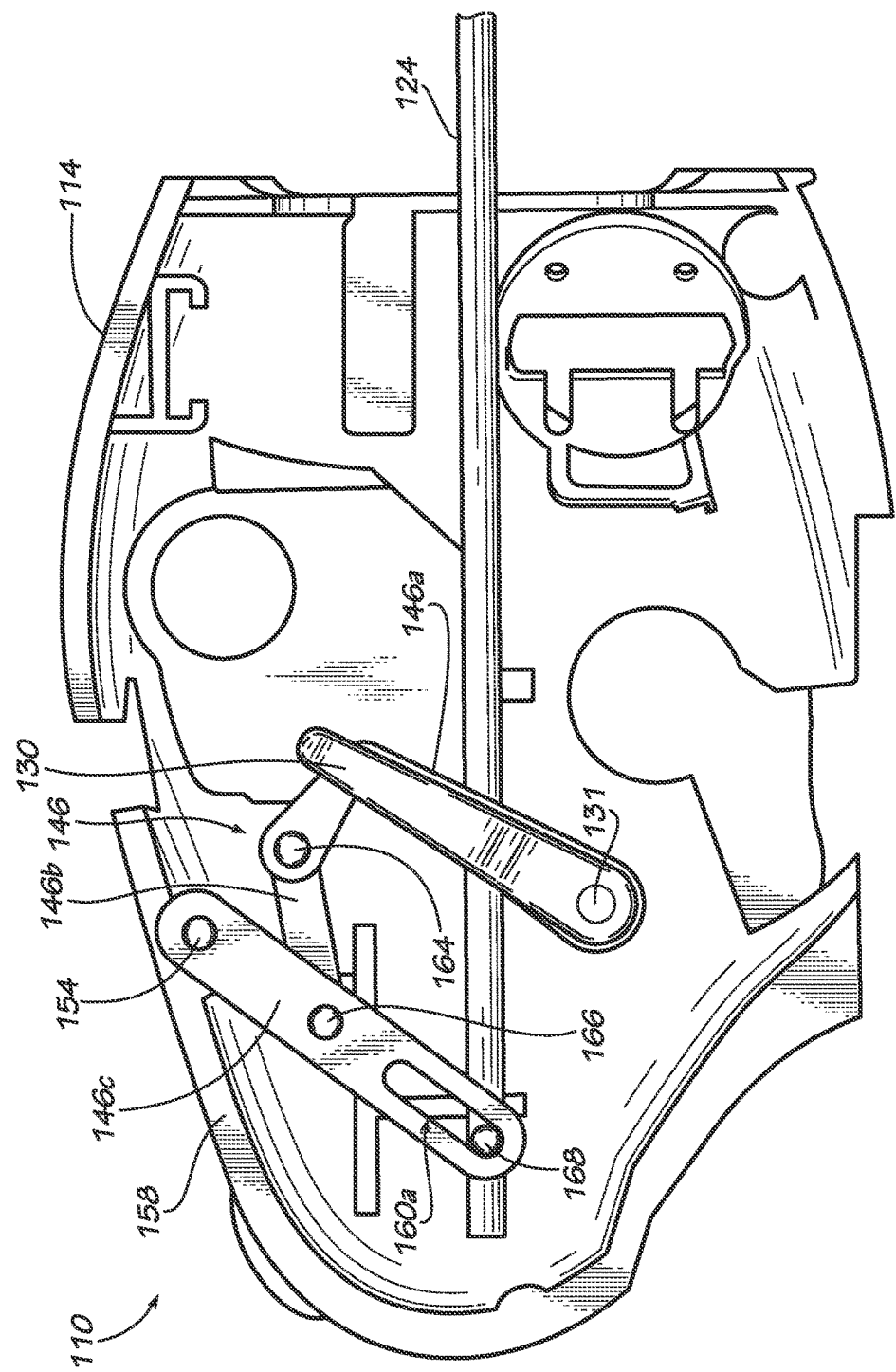
FIG. 7 is a partial, cut-away view of the proximal end of the endoscopic surgical forceps shown in FIG. 6 with the deployment mechanism shown in a retracted configuration.

The deployment mechanism 28 includes a lever 30 that is positioned within the housing 14 (FIGS. 2 and 3). The lever 30 includes a thumb paddle 32 that is operable by a user from left and/or right exterior side surfaces 14a, 14b, respectively, of the housing 14. In the illustrated embodiment, the thumb paddle 32 is disposed within opposing recesses 34 (FIGS. 1 and 4) defined on the left and right exterior side surfaces 14a, 14b of the housing 14. The thumb paddle 32 may be positioned on only one of the left or right sides side surfaces 14a, 14b of the housing 14. The thumb paddle 32 is movable within the recesses 34 relative to the housing 14 from a first configuration (FIG. 2) to second configuration (FIGS. 1, 3, and 4). In FIG. 1, the paddle 32 is shown between the first and second configurations.

Referring to FIGS. 2 and 3, a bottom portion 36 of the lever 30 is pivotably coupled to a proximal end 38 of the fixed outer shaft 12 adjacent a spring cartridge 40 of a drive assembly 42 of the forceps 10. The bottom portion 36 pivots about the outer fixed shaft 12 when the lever 30 is moved between the first and second configurations. An upper portion 44 of the lever 30 pivotably couples to a linkage 46 via one or more suitable coupling methods, e.g. a pin, rivet or the like (not explicitly shown).

Continuing with reference to FIGS. 2 and 3, the linkage 46 includes a first link member 46a and a second link member 46b. A proximal end 48 of the first link member 46a pivotably couples to the upper portion 44 of the lever 30 via one of the aforementioned coupling members (e.g., a pin, rivet, or the like.). A distal end 50 of the first link member 46a couples to a proximal end 52 of the second link member 46b via a pivot 54 (e.g., a pivot pin 54). The pivot pin 54 is slidably disposed within an elongated slot 56 defined in an interior wall 58 of the housing 14 (as best seen in FIG. 3). The elongated slot 56 has a slight curvature adjacent its distal end and extends distally into a tapered distal end of the housing 14.

In the embodiment illustrated in FIGS. 1-4, the first link member 46a also includes a slight curvature adjacent its distal end, which facilitates sliding the first link member 46a within the elongated slot 56. When the thumb paddle 32 of the lever 30 is moved from the first configuration to the second configuration, the pivot pin 54 is slid into position at a distal end of the elongated slot 56 (FIG. 3) which allows the proximal end 52 of the second link member 46b to pivot about the pivot pin 54 and move a distal end 60 of the second link member 46b distally.

The distal end 60 of the second link member 46b couples to a collar 62 via a pivot pin 64. The collar 62 is operably coupled to a proximal end 66 of the outer insulative sleeve 24 of the monopolar assembly of the forceps 10. When the proximal end 52 of the second link member 46b pivots about the pivot pin 54, the distal end 60 of the second link member 46b moves distally, which, in turn, moves the collar 62 and the outer insulative sleeve 24 distally thereby covering a pair of jaw members 21, 23 of the end effector assembly 22, as will be described in detail below.

The outer insulative sleeve 24 is slidably disposed about outer fixed shaft 12 and is configured for translation about and relative to the outer fixed shaft 12 between a fully retracted configuration (FIGS. 2 and 5A) and a fully deployed configuration (FIGS. 3, 4, and 5B). In the retracted configuration, the outer insulative sleeve 24 is disposed proximal of the end effector assembly 22, and in the deployed configuration, the outer insulative sleeve 24 is disposed about the end effector assembly 22 to substantially cover the jaw members 21, 23.

Referring to FIGS. 5A and 5B, the energizable rod member 26 is coupled to the outer insulative sleeve 24 such that advancement of the outer insulative sleeve 24 between the retracted and deployed configurations and advancement of energizable rod member 26 between the retracted and deployed configurations are effected concurrently or near concurrently, via actuation of the lever 30. Energizable rod member 26 is coupled to a source of energy for providing energy to a distal tip 25 of the energizable rod member 26, e.g., upon actuation of an activation switch 68 (FIGS. 1-4) in a monopolar mode of operation, for treating tissue using monopolar energy.

As discussed above, the forceps 10 is operable in both the bipolar mode, e.g., for grasping, treating, coagulating, sealing and/or cutting tissue, and the monopolar mode, e.g., for electrosurgical tissue treatment. In use, with respect to either mode of operation, initially, forceps 10 is manipulated such that end effector assembly 22 is positioned and oriented as desired within a surgical site.

In the bipolar mode, the outer insulative sleeve 24 and energizable rod member 26 of the monopolar assembly remain disposed in the retracted configuration, as shown in FIGS. 2 and 5A. With the jaw members 21, 23 of the end effector assembly 22 disposed in the spaced-apart configuration, the end effector assembly 22 may be maneuvered into position such that tissue to be grasped and treated is disposed between jaw members 21, 23. Next, the movable handle 17 (FIG. 1) of the handle assembly 16 is actuated, or pulled proximally relative to a fixed handle 15 (FIG. 1) such that jaw member 21 is pivoted relative to jaw member 23 from the spaced-apart configuration to the approximated configuration to grasp tissue therebetween, as shown in FIG. 5A. In this approximated configuration, energy may be selectively supplied, e.g., via activation switch 68, to tissue-sealing plates (not explicitly shown) of the jaw members 21, 23 and conducted through tissue to effect a tissue seal or otherwise treat tissue.

With respect to the monopolar mode of operation, the movable handle 17 is first depressed relative to fixed handle 15 to pivot jaw member 21 relative to jaw member 23 from the spaced-apart configuration to the approximated configuration. Once jaw members 21, 23 are disposed in the approximated configuration, the thumb paddle 32 of the lever 30 is moved from the first configuration to the second configuration, thereby urging the first and second link members 46a, 46b distally. Distal translation of the first and second link members 46a, 46b, in turn, translates the collar 36 distally through the housing 14. Distal translation of the collar 36 moves the outer insulative sleeve 24 of the monopolar assembly distally over the end effector assembly 22 and moves the energizable rod member 26 distally such that the distal tip 25 of energizable rod member 26 extends distally from both the end effector assembly 22 and the outer insulative sleeve 24 (FIG. 5B).

With the distal tip 25 of the energizable rod 26 disposed in the deployed configuration, the activation switch 68 of the forceps 10 may be selectively actuated to supply energy to the distal tip 25 of energizable rod member 26 for electrosurgically treating tissue. The distal tip 25 may also be used in a mechanical fashion depending upon the shape of the distal tip 25.

The deployment mechanism 28 described herein for use with the forceps 10 is easy to operate and inexpensive to manufacture when compared to the aforementioned conventional deployment mechanisms, as the deployment mechanism 28 is not interconnected with the handle assembly 16, rotation assembly 20 and/or the trigger assembly 18 of the forceps 10.

From the foregoing and with reference to the various figure drawings, those skilled in the art will appreciate that certain modifications can also be made to the present disclosure without departing from the scope of the same. For example, other linkage configurations may be used to move the outer sleeve 24 including the energizable rod 26 between the retracted and deployed configurations.

Referring now to FIGS. 6-9, a forceps 110 that includes a deployment mechanism 128 according an embodiment of the instant disclosure is shown. For clarity, the forceps 110 is shown without the rotation assembly, the movable handle assembly, trigger assembly, and the end effector assembly. The deployment mechanism 128 is similar to the deployment mechanism 28, thus only those features unique to the deployment mechanism 128 are described herein.

A lever 130 having a generally elongated configuration may be positioned on the left (not shown) and/or right sides 114a of the housing 114. For illustrative purposes, the lever 130 is shown positioned on the right side 114a of the housing 114. The lever 130 is configured to allow a user to selectively move the lever 130 between the first and second configurations to effect movement of an outer insulative sleeve 124 including an energizable rod, e.g., energizable rod 26.

An axle 131 supports the lever 130 and extends through an aperture (not explicitly shown) defined through the housing 114. The axle 131 is rotatable with respect to the housing 114 and connects the lever 130 to a linkage 146 including a first link member 146a, a second link member 146b, and a third link member 146c.

Figure 8:
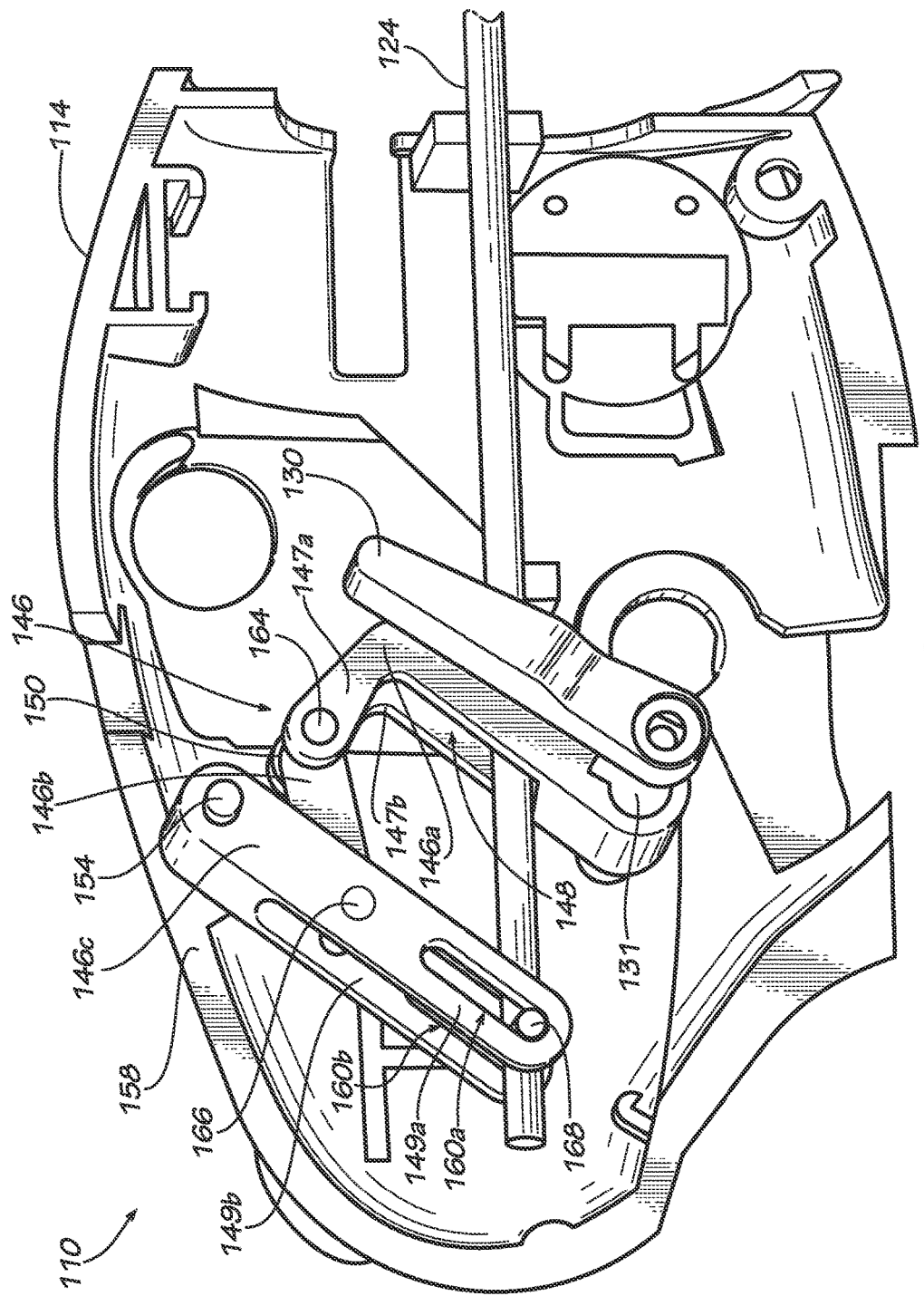
FIG. 8 is an isometric view of FIG. 7.
Figure 9:
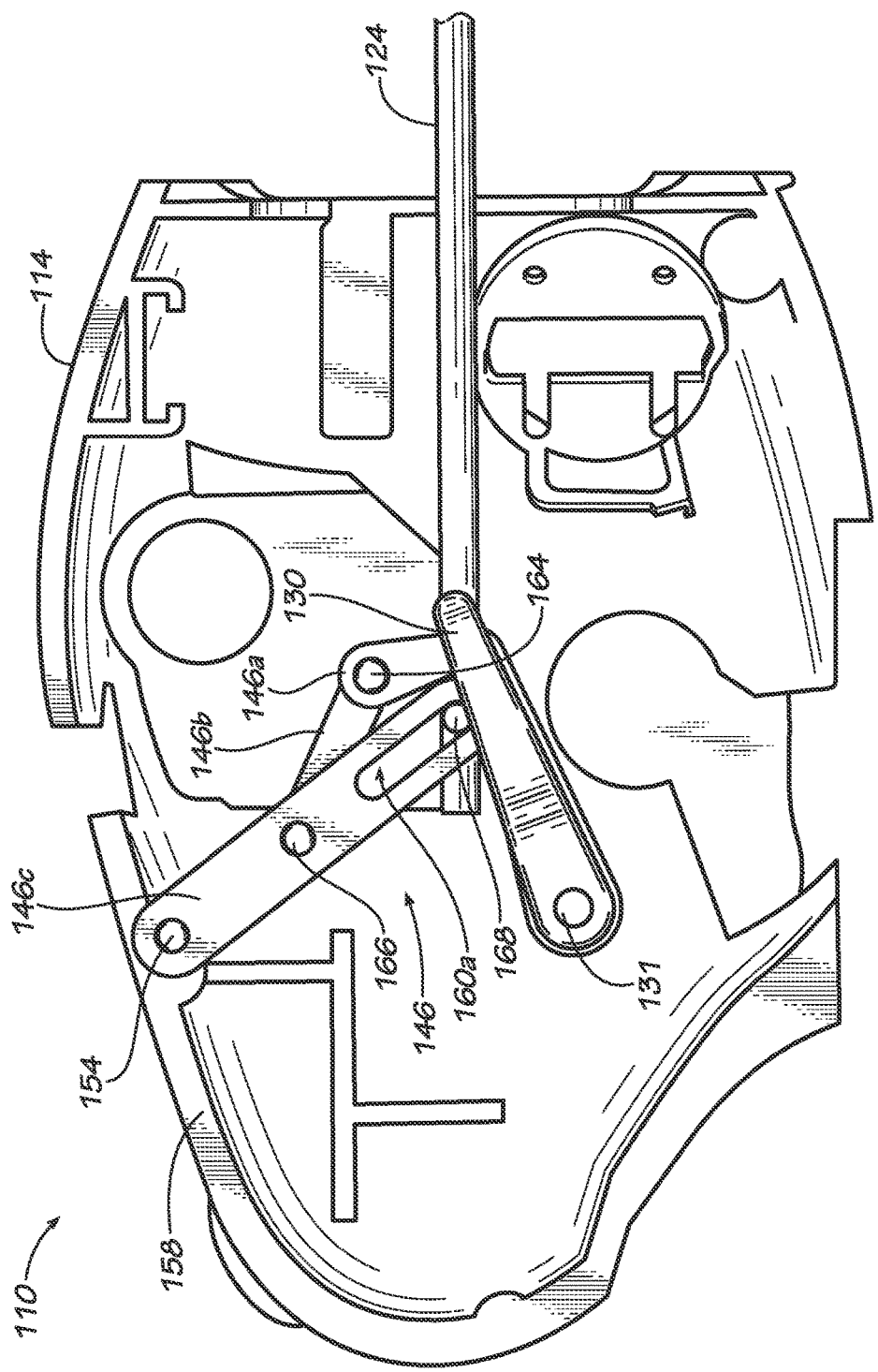
FIG. 9 is a partial, cut-away view of the proximal end of the endoscopic surgical forceps shown in FIG. 6 with the deployment mechanism of FIG. 7 shown in a deployed configuration.

The first link member 146a includes an aperture defined therein at a bottom end thereof (not explicitly shown) configured to receive the axle 131. First link member 146a is bifurcated and includes opposing finger portions 147a, 147b that extend from the bottom end of the first link member 146a and define an opening 148 therebetween configured to receive the outer insulative sleeve 124 (FIG. 8). The opening 148 allows the outer insulative sleeve 124 to translate between the opposing finger portions 147a, 147b when the lever 130 is moved between the first and second configurations.

The second link member 146b includes an aperture (not explicitly shown) at a distal end 150 thereof that, along with apertures (not explicitly shown) defined through top portions of the opposing finger portions 147a, 147b, are configured to receive a pivot pin 164. The pivot pin 164 connects the distal end 150 of the second link member 146b to the opposing finger portions 147a, 147b of the first link member 146a.

The second link member 146b includes at its proximal end an aperture (not explicitly shown) defined therein that, along with apertures (not explicitly shown) defined through opposing finger portions 149a, 149b of the third link member 146c, are configured to receive a pivot pin 166. The pivot pin 166 connects the proximal end of the second link member 146b to the opposing finger portions 149a, 149b of the third link member 146c.

The third link member 146c includes a detent 154 at a top end thereof that is rotatably seated within a corresponding indent (not explicitly shown) defined within an interior wall portion 158 of the housing 114. This indent and detent configuration allows the third link member 146c to rotate in relation to the interior wall 158 of the housing 114 when the lever 130 is moved between the first and second configurations.

A pair of elongated slots 160a, 160b are defined through the opposing finger portions 149a, 149b of the third link member 146c and are configured receive a pivot pin 168 positioned on the outer insulative sleeve 124. The pivot pin 168 couples to the proximal end of the outer insulative sleeve 124 and extends transversely in relation to the longitudinal axis "A-A."

In use, once the jaw members 21, 23 are disposed in the approximated configuration, the lever 130 is moved from the first configuration to the second configuration, thereby urging the first, second, and third link members 146a, 146b, 146c distally. Distal translation of the first, second, and third link members 146a, 146b, 146c, in turn, moves the outer insulative sleeve 124 and the energizable rod member 126 in a manner as described above with respect to the outer insulative sleeve 24 and the energizable rod member 26 (see FIG. 9).

Figure 10:
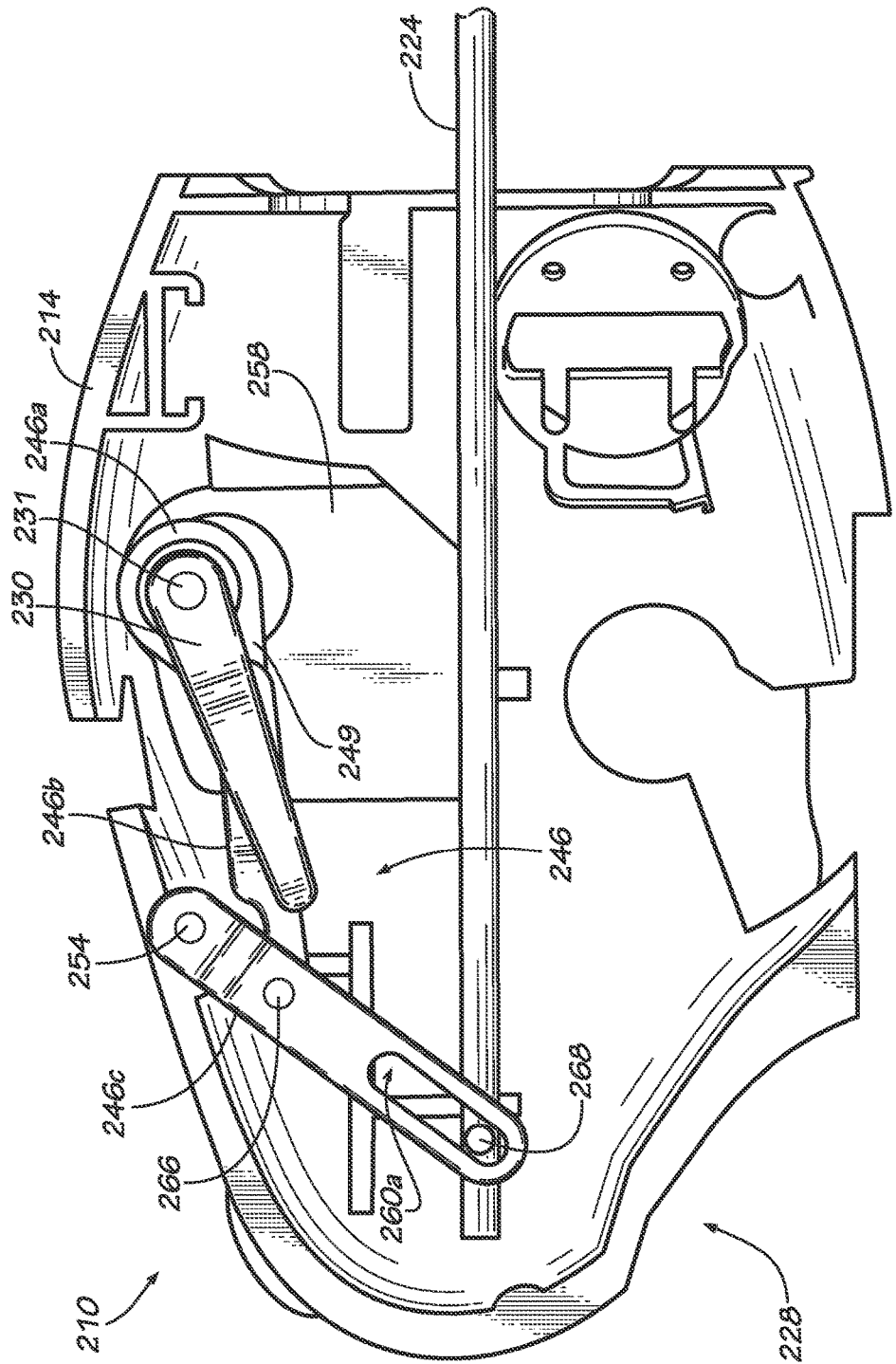
FIG. 10 is a partial, perspective view of a proximal end of an endoscopic surgical forceps including a deployment mechanism in accordance with yet another embodiment of the present disclosure.
Figure 11:
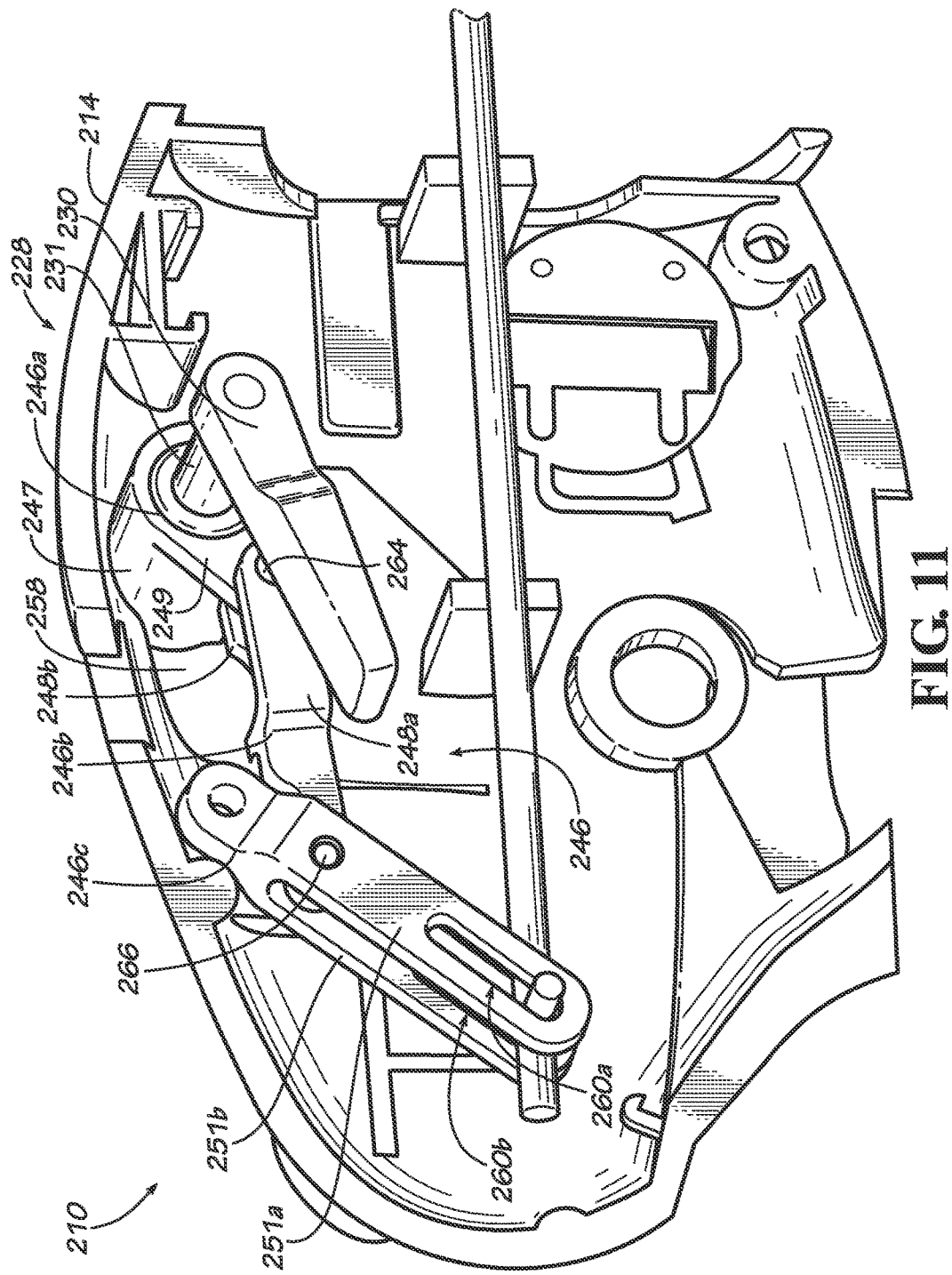
FIG. 11 is an isometric view of FIG. 10.
Figure 12:
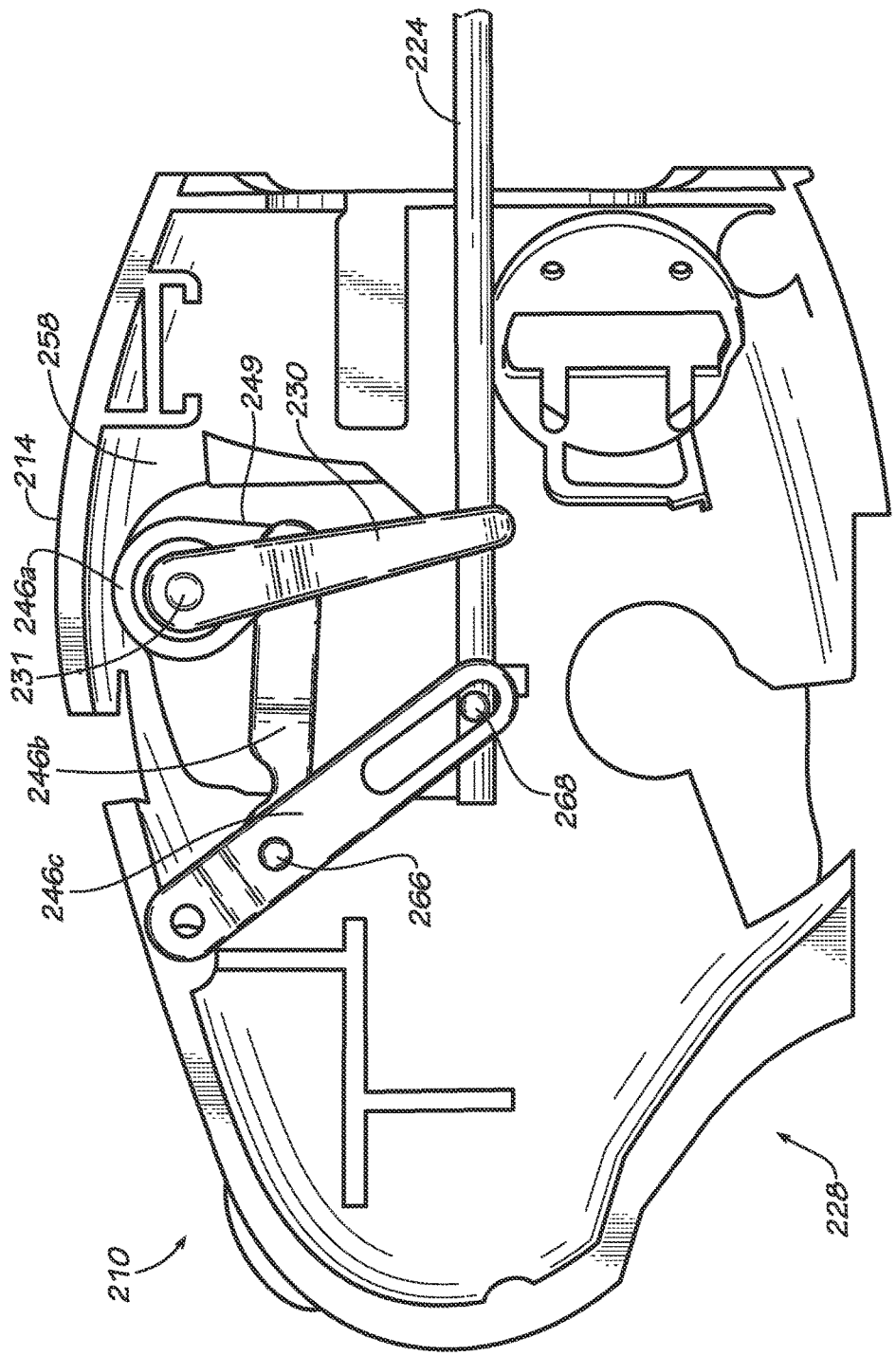
FIG. 12 is a partial, cut-away view of the proximal end of the endoscopic surgical forceps shown in FIG. 10 with the deployment mechanism shown in a deployed configuration.

FIGS. 10-12 illustrate a forceps 210 that includes a deployment mechanism 228 according yet another embodiment of the instant disclosure. Deployment mechanism 228 is similar to deployment mechanism 128 and, accordingly, only those features unique to the deployment mechanism 228 are described herein.

A lever 230 having a generally elongated configuration is disposed on the left and/or right sides of the housing 214. For illustrative purposes, the lever 230 is shown for actuation from the right side of the housing 214. The lever 230 is configured to allow a user to move the lever 230 between the first and second configurations to effect movement of an outer insulative sleeve 224 including an energizable rod, e.g., the energizable rod 26.

The lever 230 includes an axle 231 at a top end thereof that extends through an aperture (not explicitly shown) defined through the housing 214. The axle 231 is rotatable with respect to the housing 214 and connects the lever 230 to a linkage assembly 246 including a first link member 246a, a second link member 246b, and a third link member 246c.

Referring to FIG. 11, the first link member 246a includes a body portion 247 having a cylindrical configuration. The body portion 247 rotatably seats within a corresponding cylindrical aperture (not explicitly shown) defined within an interior wall portion 258 of the housing 214. The body portion 247 includes an aperture (not explicitly shown) that receives the axle 231 of the lever 230 to secure the lever 230 to the body portion 247 of the first link member 246a. The body portion 247 also includes a flange 249 that is positioned between opposing wall portions 248a, 248b provided at a distal end of the second link member 246b.

The opposing wall portions 248a, 248b have apertures (not explicitly shown) that, along with an aperture (not explicitly shown) defined through the flange 249, receive a pivot pin 264 that connects the wall portions 248a, 248b of the second link member 246b to the flange 249 of the first link member 246a.

The second link member 246b includes an aperture (not explicitly shown) at a proximal end thereof that, along with apertures (not explicitly shown) defined through opposing finger portions 251a, 251b of the third link member 246c, receive a pivot pin 266 that connects the proximal end of the second link member 246b to the opposing finger portions 251a, 251b of the third link member 246c.

The third link member 246c includes a detent 254 at a top end thereof that couples to a corresponding indent (not explicitly shown) defined within the interior wall portion 258 of the housing 214. This indent and detent configuration allows the third link member 246c to rotate in relation to the interior wall 258 of the housing 214 when the lever 230 is moved between the first and second configurations.

Elongated slots 260a, 260b are defined through the opposing finger portions 251a, 251b of the third link member 246c and are configured to receive a pivot pin 268 disposed on the outer insulative sleeve 224. The pivot pin 268 couples to a proximal end of the outer insulative sleeve 224 and extends transversely in relation to the longitudinal axis "A-A."

In use, once the jaw members 21, 23 are disposed in the approximated configuration, the lever 230 is moved from the first configuration to the second configuration, thereby urging the first, second, and third link members 246a, 246b, 246c distally. Distal translation of the first, second, and third link members 246a, 246b, 246c, in turn, moves the outer insulative sleeve 224 and of the energizable rod member 26 in a manner as described above with respect to the outer insulative sleeve 24 and the energizable rod member 26.

It is noted that the aforementioned advantages described with respect to the deployment mechanism 28 configured for use with the forceps 10 are attainable also with the deployment mechanisms 128, 228.

The various embodiments disclosed herein may also be configured to work with robotic surgical systems and what is commonly referred to as "Telesurgery". Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument, comprising:
   a housing;
   a shaft extending distally from the housing having an end effector assembly attached at a distal end thereof;
   a handle assembly coupled to the housing, the handle assembly including a movable handle operable to manipulate the end effector assembly;
   an outer sleeve disposed about the shaft and selectively translatable relative thereto;
   an energizable member operably coupled to the outer sleeve; and
   a deployment mechanism operably coupled to the housing, the deployment mechanism including:
   a lever rotatably coupled to the housing and positioned proximally of the movable handle; and
   at least one link member coupled between the lever and the outer sleeve, the at least one link member coupled to the outer sleeve distally of the movable handle,
   wherein rotation of the lever relative to the housing moves the at least one link member, which, in turn, translates the outer sleeve distally to move the outer sleeve over the end effector assembly and simultaneously deploy the energizable member distally past the end effector assembly.

2. The electrosurgical instrument according to claim 1, further comprising a collar operably disposed on a proximal end of the outer sleeve, the collar pivotably coupled to the at least one link member.

3. The electrosurgical instrument according to claim 2, wherein the at least one link member includes first and second link members and wherein a first pivot pin pivotably couples a distal end of the second link member to the collar of the outer sleeve.

4. The electrosurgical instrument according to claim 3, wherein a proximal end of the first link member is pivotably coupled to the lever and a distal end of the first link is pivotably coupled to a proximal end of the second link member via a second pivot pin.

5. The electrosurgical instrument according to claim 4, wherein an elongated slot defined in the housing extends from an interior wall of the housing and operably receives the second pivot pin.

6. The electrosurgical instrument according to claim 5, wherein the second pivot pin translates within the elongated slot when the lever is rotated relative to the housing to guide movement of the first and second link members.

7. The electrosurgical instrument according to claim 1, wherein the lever is rotatable between a first configuration, wherein the outer sleeve and energizable member are disposed in retracted positions, and a second configuration, wherein the outer sleeve and energizable member are disposed in deployed positions.

8. The electrosurgical instrument according to claim 1, wherein the lever includes a body portion disposed within the housing and a paddle portion extending from the body portion through an opening in the housing to permit manipulation thereof from an exterior of the housing.

9. The electrosurgical instrument according to claim 1, wherein the end effector assembly is configured for treating the tissue with bipolar energy and wherein the energizable member is configured for treating tissue with monopolar energy.

10. An electrosurgical instrument, comprising:
a housing;
a shaft extending distally from the housing having an end effector assembly attached at a distal end thereof;
an outer sleeve disposed about the shaft and selectively translatable relative thereto;
an energizable member operably coupled to the outer sleeve; and
a deployment mechanism operably coupled to the housing, the deployment mechanism including:
a lever rotatably coupled to the housing via an axle;
a first link member pivotably coupled to the axle at a fixed end thereof and defining a free end;
a second link member pivotably coupled to the housing at a fixed end thereof and coupled to the deployable assembly at a free end thereof, the second link member defining an intermediate portion disposed between the fixed and free ends; and
a third link member pivotably coupled between the fixed end of the first link member and the intermediate portion of the second link member,
wherein rotation of the lever about the axle pivots the first and second link members about the respective fixed ends thereof and effects movement of the third link member, thereby translating the outer sleeve distally over the end effector assembly and simultaneously deploying the energizable member distally past the end effector assembly.

11. The electrosurgical instrument according to claim 10, wherein the first link member includes a bifurcated configuration having an opening defined therein configured to receive the outer sleeve therebetween.

12. The electrosurgical instrument according to claim 10, wherein the second link member includes a bifurcated configuration having opposing finger portions each defining an elongated slot configured to receive at least a portion of a pivot pin coupled to the outer sleeve.

13. The electrosurgical instrument according to claim 10, wherein the lever is rotatable between a first configuration, wherein the outer sleeve and energizable member are disposed in retracted positions, and a second configuration, wherein the outer sleeve and energizable member are disposed in deployed positions.

14. The electrosurgical instrument according to claim 10, wherein the end effector assembly is configured for treating tissue with bipolar energy and wherein the energizable member is configured for treating the tissue with monopolar energy.

15. The electrosurgical instrument according to claim 10, wherein the lever includes a body portion disposed within the housing and a paddle portion extending from the body portion through an opening in the housing to permit manipulation thereof from an exterior of the housing.

16. An electrosurgical instrument, comprising:
a housing;
a shaft extending distally from the housing having an end effector assembly attached at a distal end thereof;
an outer sleeve disposed about the shaft and selectively translatable relative thereto;
an energizable member operably coupled to the outer sleeve; and
a deployment mechanism operably coupled to the housing, the deployment mechanism including:
a lever rotatably coupled to the housing via an axle;
a first link member pivotably coupled to the axle at a fixed end thereof and defining a free end; and
a second link member pivotably coupled to the housing at a fixed end thereof and coupled to the deployable assembly at a free end thereof, the second link member defining an intermediate portion disposed between the fixed and free ends, the free end of the first link member pivotably coupled to the intermediate portion of the second link member,
wherein rotation of the lever about the axle pivots the first and second link members about the respective fixed ends thereof, thereby translating the outer sleeve distally over the end effector assembly and simultaneously deploying the energizable member distally past the end effector assembly.

17. The electrosurgical instrument according to claim 16, wherein the second link member includes a bifurcated configuration having opposing finger portions each defining an elongated slot configured to receive at least a portion of a pivot pin coupled to the outer sleeve.

18. The electrosurgical instrument according to claim 16, wherein the lever is rotatable between a first configuration, wherein the outer sleeve and energizable member are disposed in retracted positions, and a second configuration, wherein the outer sleeve and energizable member are disposed in deployed positions.

19. The electrosurgical instrument according to claim 16, wherein the lever includes a body portion disposed within the housing and a paddle portion extending from the body portion through an opening in the housing to permit manipulation thereof from an exterior of the housing.

20. The electrosurgical instrument according to claim 16, wherein the end effector assembly is configured for treating tissue with bipolar energy and wherein the energizable member is configured for treating the tissue with monopolar energy.

* * * * *